United States Patent
Zhang et al.

(10) Patent No.: US 11,653,997 B2
(45) Date of Patent: May 23, 2023

(54) DOCKING DEVICE, SURGICAL HOLDING DEVICE, AND METHOD

(71) Applicant: KARL STORZ SE & Co. KG, Tuttlingen (DE)

(72) Inventors: Yaokun Zhang, Tuttlingen (DE); Kirsten Klein, Tuttlingen (DE); Johannes Fallert, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 228 days.

(21) Appl. No.: 17/173,621

(22) Filed: Feb. 11, 2021

(65) Prior Publication Data
US 2021/0282891 A1 Sep. 16, 2021

(30) Foreign Application Priority Data

Mar. 12, 2020 (DE) ...................... 10 2020 106 817.4

(51) Int. Cl.
*A61B 90/57* (2016.01)
*A61B 34/30* (2016.01)
(Continued)

(52) U.S. Cl.
CPC .......... *A61B 90/57* (2016.02); *A61B 17/3476* (2013.01); *A61B 34/30* (2016.02); (Continued)

(58) Field of Classification Search
CPC ..... A61B 90/57; A61B 34/30; A61B 17/3476; A61B 2017/00486; A61B 2560/0456
See application file for complete search history.

(56) References Cited

U.S. PATENT DOCUMENTS 6,201,984 B1   3/2001 Funda et al.
8,230,863 B2 * 7/2012 Ravikumar ............ A61B 90/50
                                                                          403/56
(Continued)

FOREIGN PATENT DOCUMENTS

DE   102014116103 A1   5/2016
EP   2 246 006 A2      11/2010
(Continued)

OTHER PUBLICATIONS

Office Action, DE 10 2020 106 817.4, dated Jan. 14, 2021 (in German) (13 pp.).
(Continued)

*Primary Examiner* — Anita M King
(74) *Attorney, Agent, or Firm* — Eversheds Sutherland (US) LLP

(57) ABSTRACT

The present application provides a docking device, a surgical holding device having such a docking device, and a method for connecting a surgical instrument to a holding arm of a surgical holding device. The docking device has a two-part adapter device connected at a proximal end to the holding arm and at a distal end to the surgical instrument, a first adapter with an elongated portion with a longitudinal axis and a connecting body present at a distal end of the first adapter, and a first engagement element with a terminal connection surface. The adapter device has a second adapter on the shaft of the surgical instrument and an engagement element facing the terminal connection surface in the docking situation. The terminal connection surface of the first adapter is inclined at a predetermined first angle in relation to its longitudinal axis, which is in a range from 30° to 90°.

17 Claims, 12 Drawing Sheets

(51) Int. Cl.
*A61B 17/34* (2006.01)
*A61B 17/00* (2006.01)

(52) U.S. Cl.
CPC ............... *A61B 2017/00486* (2013.01); *A61B 2560/0456* (2013.01)

(56) References Cited

U.S. PATENT DOCUMENTS

| | | | | |
|---|---|---|---|---|
| 8,313,070 | B2 * | 11/2012 | Kronner | A61B 90/57 |
| | | | | 248/231.51 |
| 10,959,605 | B2 * | 3/2021 | Huber | A61B 17/3478 |
| 11,471,243 | B2 * | 10/2022 | Silver | A61B 90/30 |
| 2005/0272981 | A1 * | 12/2005 | Bjork | A61B 90/57 |
| | | | | 600/227 |
| 2006/0200005 | A1 * | 9/2006 | Bjork | A61B 1/00149 |
| | | | | 600/227 |
| 2020/0306001 | A1 * | 10/2020 | Silver | A61B 90/57 |
| 2021/0113241 | A1 * | 4/2021 | Forster | A61B 17/3468 |

FOREIGN PATENT DOCUMENTS

| | | |
|---|---|---|
| JP | 2006061272 A | 3/2006 |
| WO | 2019005921 A1 | 1/2019 |
| WO | 2019096929 A1 | 5/2019 |
| WO | 2019136062 A1 | 7/2019 |

OTHER PUBLICATIONS

Arash Sanagoo, Eine neuartige Roboterkinematik fur die laparoskopische Single-Port Chirurgie, Fraunhofer Verlag, 2015 (208 pp.). (in German).

* cited by examiner

DOCKING DEVICE, SURGICAL HOLDING DEVICE, AND METHOD

TECHNICAL FIELD

The invention relates to a docking device, to a method for connecting a surgical instrument to a holding arm of a surgical holding device, and to a surgical holding device having such a docking device.

BACKGROUND OF THE INVENTION

Assistance systems are increasingly being used when surgical procedures are performed, in order to relieve the medical staff, and so that operations are performed reliably and with the least impact on the patient. From the prior art, it is known to use surgical holding devices, including surgical robots, for holding and positioning surgical instruments. With these, actions can be performed on the patient's body via tools connected to them. In this case it is conventional for the surgical instrument to first be placed within the body of a patient before it is connected to the holding device.

EP 2 246 006 A2 describes an operation assistance system in which a surgical instrument, such as an endoscope, is connected to an arm of a robot to allow moving it via the robot's kinematics. For this purpose, an instrument carrier is provided which is releasably connected to a kinematic arm via a pivot link, and which is further connected to an instrument holder via a pivot link. The surgical instrument is snapped onto this instrument holder. In this case, no pre-positioning is undertaken which is favorable for the subsequent procedure.

DE 10 2014 116 103 A1 discloses an operation assistance system that comprises a plurality of robot arms which each map pivot axes that extend in different directions. The robot arms are connected to each other at their ends, wherein a support column carries a first robot arm, and a second robot arm is connected to the latter with articulation. At a free end of the second robot arm, a link piece is inserted which is connected to an instrument carrier with which an endoscope can be coupled. There is no pre-positioning of the endoscope being coupled.

In other devices, the surgical instrument with which work will be carried out on a body, or the trocar in which it is guided, is clamped directly to the holding arm or robot head. In both cases, the clamping of the instrument involves strong movements of the instrument; repositioning can damage the entry point of the body, which can be even worse if the pivot point is not precisely registered.

In microsurgical, and in particular laparoscopic, operations, in which access for the microsurgical instrument is created via a trocar placed in the patient's abdominal wall, the trocar point—that is, the center of the trocar in the abdominal wall—forms a pivot point around which the instrument can be moved, and which itself must be fixed to be as immobile as possible in order to place the least possible stress on the patient's tissue. It is therefore necessary, especially with driven kinematics, to register this pivot point in the control system so that, when movements are transferred to the surgical instrument in order to position it in the desired manner in the patient's body, the movements can be coordinated accordingly around the fixed pivot point.

EP 2 254 735 B1 describes an advance registration, by means of a register button, of a planned trocar point as the zero point of a coordinate system for an operation assistance system. After that, however, the trocar must either be placed free-hand or using templates or projections at the planned, registered point, which is not precise and also does not correspond to the natural workflow.

In some cases, the pivot point can be set first and subsequently registered. There are trocars for this purpose, the position of which is captured via two mutually perpendicular laser lines that are projected onto the abdominal wall and that have to be moved to the trocar point, wherein the third dimension is only detectable by depth markings provided on the trocar. It is also possible to manually move a measuring tip mounted on the robot to the trocar point, and trigger a registration at this point, as disclosed in U.S. Pat. No. 6,201,984 B1—which also describes the further movement and positioning of a trocar at one end of a robot holding arm. However, this workflow is also complex and prone to errors.

SUMMARY OF THE INVENTION

Proceeding from this prior art, the object of the present invention is to provide a low-impact option, which is adapted to the usual workflow before and during a surgical procedure, of connecting a surgical instrument to a holding arm and holding it stably in the patient's body.

This object is achieved by a docking device having the features in accordance with claim 1.

The further object of favorably pre-positioning a surgical instrument for a surgical procedure and being able to move a correctly registered pivot point is achieved by the surgical holding device having the features of claim 10.

Yet another object is to quickly connect a surgical instrument in a low-impact manner to a holding arm of a surgical holding device in an orientation which is suitable for operation. This object is achieved by the method having the features of independent claim 13.

Further refinements are set out in the respective dependent claims.

A first embodiment of a docking device, which is designed to connect a surgical instrument to a holding arm of a surgical holding device in a docking situation, has a two-part adapter device. The latter is designed in such a manner that it can be connected at its proximal end to the holding arm and at its distal end to the surgical instrument. The surgical instrument has a rod-shaped shaft and a handle adjoining it proximally, and is designed to be guided through a trocar. The two-part adapter device has a first adapter with an elongated portion, with a corresponding longitudinal axis. The first adapter also has a connecting body. The connecting body is situated at a distal end of the first adapter and has a first engagement element with a terminal connection surface. The two-part adapter device also has a second adapter. The second adapter is designed to be arranged on the shaft of the surgical instrument. It has an engagement element which points, in the docking situation, towards the terminal connection surface, and which corresponds to said terminal connection surface. The connecting body of the first adapter forms, in the docking situation, a releasable connection with the corresponding engagement element of the second adapter. The terminal connection surface of the first adapter is inclined with respect to its longitudinal axis by a predetermined first angle, which is in a range from 30° to 90°.

In a further embodiment of the embodiment according to the invention, the angle of inclination can be in a range from 45° to 75°, preferably in a range from 55° to 65°, and very particularly preferably 60°

The terms "proximal" and "distal" relate to the position with respect to the operator, such that "proximal" means closer to the operator and "distal" means further away from the operator.

The state in which the holding arm is completely connected to the surgical instrument via the docking device according to the invention is referred to as the "docking situation," and at the same time constitutes the starting situation for using the surgical instrument in a subsequent surgical procedure.

The term surgical holding device refers to both passive holding devices which simply hold the surgical instrument in a preset position, and to active holding devices via which the surgical instrument can also be operated—in particular, repositioned; this also includes complete surgical robots with which surgical procedures can also be carried out remotely. The surgical instrument can in particular be a laparoscope; in general, this also includes other surgical instruments that are used in microsurgery and in particular in laparoscopy.

The second adapter of the two-part adapter device is advantageously attached directly to the surgical instrument, which can be done in advance in preparation for a surgical procedure. This then makes it significantly easier to couple the instrument, which is already provided with the second adapter, to the first adapter, since only the first engagement element has to be connected to the corresponding engagement element. This requires little effort and, in particular, involves the least possible movement of the instrument itself; consequently, the patient's tissue is stressed very little. The inclination of the terminal connection surface has this advantage in particular compared to the prior art, as constituted by DE 10 2014 116 103 A1 and EP 2 246 006 A2, both of which have horizontal connection surfaces between holding components, wherein the maintenance of the pivot point at the puncture point of the trocar is not particularly emphasized. With the solution according to the invention, an endoscope can be connected to the holding arm directly and in a targeted manner while maintaining the fixed pivot point.

The connecting body of the first adapter can form the first engagement element in its entirety, or solely with part of the connecting body—or the first engagement element is arranged thereon. As such, by bringing the first engagement element of the first adapter into engagement with the corresponding engagement element of the second adapter, a connection can be established which can be released without the aid of a tool.

The terminal connection surface, inclined at the predetermined first angle—which means the smallest angle formed between the longitudinal axis of the elongated portion of the first adapter and the terminal connection surface of the first adapter—ultimately determines the orientation of the shaft of the surgical instrument. "Terminal" indicates the distal end of the first adapter, and thus the side of the connecting body which is oriented away from the elongated portion. When the connection between the first and second adapter is established, the corresponding engagement element of the second adapter is aligned to correspond with the terminal connection surface, and consequently also the surgical instrument. In this way, the surgical instrument can advantageously be cleverly pre-positioned for a surgical procedure. In this context, "predetermined" means that docking devices with greater or smaller first angles can advantageously be provided depending on the desired docking situation to be created—which can depend, for example, on the type of surgical procedure or the type of surgical instrument.

In a further embodiment, the connecting body with the portion having the connection surface is designed as a slide. The corresponding engagement element of the second adapter is accordingly designed as a rail element for receiving the slide. This means that the first and second adapters are connected via a movement parallel to the connection surface, and parallel to the longitudinal axis of the rail element. The slide can have a trapezoidal or dovetail-shaped cross-section, for example, and the rail element can have a corresponding trapezoidal or dovetail contour, such that a positive connection is created. Of course, other geometries and/or engagement cross-sections other than the dovetail shape and the corresponding negative for the slide and rail, known to the person skilled in the art, can also be selected. The slide and rail are flat, preferably with a height of only a few millimeters, up to one centimeter.

In a further embodiment of the adapter device according to the invention, the connecting body of the first adapter has a first opening. The opening or its edges can be beveled, cut or inclined at an angle that corresponds to the first angle of the terminal connection surface with respect to the longitudinal axis of the first adapter. In other words, an imaginary axis runs through the first opening parallel to the longitudinal axis of the rail element and thus, in the docking situation, parallel to the longitudinal axis of the surgical instrument and/or to its shaft.

The first opening can be shaped as a hole in the wall of the connecting body, or as a through-opening, or as a cylindrical recess, the orientation of which runs parallel to the terminal connection surface.

The first opening is used to allow a laser beam, which is also to be understood as a bundle of parallel laser beams, to exit from a laser device at the first angle, which laser device is arranged at the opening. If the opening belongs to a cylindrical recess, this can house the laser device.

In addition, the elongated portion of the first adapter has a second opening which is inclined at a second angle with respect to the longitudinal axis of the first adapter. The second opening can also be a "hole," optionally with edges beveled at an angle, in the wall of the first adapter or in the shell surface of a cylindrical body of the adapter, or a cylindrical recess therein (optionally also beveled), and can likewise form a receptacle for a second laser device. The second opening also serves to allow a laser beam to exit the second laser device at the second angle.

The second angle is smaller than the first angle and lies in a range from 20° to 80°. Imaginary axes along these angles are aligned in such a way that they intersect at a predetermined point of intersection which is defined by the first and second angle and the distance of the two openings from each other, measured along the longitudinal axis of the elongated portion of the first adapter; as a result, said point of intersection is "predetermined" to the extent that it is specified by the shaft length of the surgical instrument to be connected.

The openings from which laser light can exit can also have transparent windows for the laser light used. The openings are therefore designed so that laser devices can emit laser beams emitting from the first adapter at the corresponding angles, both of which intersect at a predetermined intersection which corresponds to the pivot point in an operating arrangement of the docking device.

The point at which the laser beams intersect from the two openings also defines the distance between the intersection point and the docking device, and consequently the holding arm.

Each of the laser devices can be a laser fiber that can be connected to a laser beam source. The laser beam source can certainly be located outside the docking device, such that only the fibers that allow laser light to exit at the opening are guided inside the adapter.

The laser devices in this case could alternatively also be laser modules with their own laser beam source, which generate the laser beam themselves.

The windows that close the openings are advantageously diffractive elements that allow each of the laser beams to emerge in the shape of a cross, for example.

The "pivot point" is the fixed point in space in which the trocar is held. The trocar or the surgical instrument can be pivoted about this pivot point. Translation along the longitudinal axis of the shaft and rotation around it are possible independently of this. In a surgical procedure, a target pivot point is specified by the trocar point—the puncture point of the trocar to be introduced in a body. The latter can be, in the abstract, any solid volume, but in practice, it is the patient's body tissue. However, this point is shifted if the movement of the surgical instrument is not correctly coordinated with this target pivot point, such that injuries can occur to the tissue around the puncture site. The docking device according to the invention advantageously prevents this because the predetermined intersection point can be aligned in such a manner that it lies in the pivot point of the trocar through which the held surgical instrument is guided. As a result, a predetermined distance (dependent on the length of the shaft of the surgical instrument) is set between the holding arm and the pivot point. The surgical instrument has a fixed length, and the pivot point is determined according to this fixed length. As a result, after the connection has been completed, the surgical instrument can be moved about this pivot point.

According to a further embodiment, the first opening adjoins the terminal connection surface. As such, the smallest possible distance is achieved between the first opening and the shaft of the surgical instrument connected to the second adapter, such that the first laser beam emanating from the first laser device is not only parallel, but also runs with only a slight offset to the longitudinal axis of the shaft of the surgical instrument in the docking situation.

This is also made possible by the flat design of the slide and rail, such that the instrument axis is as close as possible to the laser axis of the first laser device.

In a further embodiment, at least one electrical connection line can be present in the first adapter and at least one electrical contact surface for the laser device(s) and/or the second adapter can be present on the surface of the proximal end and/or distal end of the first adapter.

It is conceivable that there is one electrical connection line and an electrical contact surface for each laser device.

In a further embodiment of the docking device according to the invention, the second adapter has a tubular portion in addition to the corresponding engagement element, wherein the corresponding engagement element of the second adapter is arranged above the tubular portion of the second adapter in the docking situation. The tubular portion has a cylindrical passage opening through which the shaft of the surgical instrument can be guided, the passage opening being only slightly larger in diameter than the diameter of the shaft so that it has as little play as possible in the passage opening. The longitudinal axis of the cylindrical passage opening of the tubular portion runs parallel to the corresponding engagement element, such that, after the second adapter has been arranged on the shaft of the surgical instrument, a movement of the second adapter along the axis of the rail element corresponds to a movement of the shaft along its axis. A movement which connects the two adapters along the longitudinal axis of the shaft of the surgical instrument has proven to be particularly advantageous and gentle, since it uses the degree of freedom that is already available in a surgical instrument guided by a trocar, and the operator can see both the adapter and the solid volume in which the trocar is placed—for example, a patient—at the same time.

In general, the handling of the adapter and thus the docking device should be understood technically and mechanically in relation to any solid volume that has the pivot point; the handling represents a purely technical-mechanical process.

Furthermore, the tubular portion of the second adapter can have a coupling element which can be coupled to a corresponding coupling element at the proximal end of the shaft of the surgical instrument so that the second adapter cannot slip off the shaft. Alternatively or in addition, the second adapter can also be screwed in/on, clamped on or glued on.

In yet another embodiment, the first adapter has at its proximal end a second engagement element which is designed to be releasably connected to a corresponding engagement element of the holding arm. So that such a direct connection of the first adapter is possible, the connection point of the intended holding arm with respect to the connection mechanism must be known, as must the dimensions, so that the proximal end of the first adapter can be adapted to it. This is usually the case with approved assistance systems.

Yet another embodiment provides that the first adapter advantageously has a holding cone at the proximal end of the first adapter, which tapers towards a proximal tip. This holding cone can not only constitute a second engagement element that can be brought into engagement with a corresponding engagement element of the holding arm or another corresponding connecting piece; it is also shaped so that it can pierce a sterile cover (drape) surrounding the holding arm with its tip.

It is not necessary to pierce an existing sterile drape if only mechanical holding will be performed, without signal transmission, or if the drape has a special signal transmission adapter for arrangement on a robot head, such that the barrier formed by the drape can be retained. It is then sufficient if a gap remains between the second engagement element of the first adapter and the holding arm.

In a further embodiment, the docking device has a flange piece which is designed to be arranged on a corresponding mating flange of the holding arm. The mating flange can be a standard flange of the holding arm, the shape of which is known to the person skilled in the art for the design of the flange piece of the docking device for arrangement thereon; a screw connection can be sufficient. The flange piece makes it possible to design the proximal end of the first adapter in any desired manner, without being tied to the shape of the existing connection options of the holding arm; the flange piece will be formed to correspond thereto. In a preferred embodiment, the flange piece has a conical recess for this purpose, which, for receiving the holding cone of the first adapter, corresponds to an outer circumferential shape of the holding cone. A gap can also remain between the flange piece and the holding cone, which gap is just wide enough to receive and clamp a sterile drape in it in one layer. In a further embodiment, the holding cone can be present on the flange piece and the proximal end of the first adapter has the recess in which the holding cone can be received.

All connections that can be made with the docking device according to the invention—that is, between the first adapter and the holding arm or the flange piece arranged on the holding arm, between the first adapter and the second adapter, and between the second adapter and the surgical instrument—can be made manually and can also be released manually.

In further embodiments, these connections are formed using alignment elements, and in such a manner that the mutually connectable, mutually corresponding elements can only be brought into engagement in a clear orientation.

The docking device according to the invention can be designed as a single-use product. It can also be completely or partially—in particular, the two adapters of the two-part adapter device—sterilizable, preferably autoclavable.

The invention also relates to a surgical holding device having at least one holding arm, which can be connected to a surgical instrument via the docking device according to the invention, or is connected to it in the docking situation. As described above, the surgical instrument has a rod-shaped shaft and a handle and is designed to be guided through a trocar. In the docking situation, the surgical instrument is advantageously connected to the surgical holding device in such a way that it is expediently pre-positioned for a surgical procedure. It may be sufficient if the holding device only holds the surgical instrument in this preset position. However, the surgical instrument can also be moved via the holding device; this includes both manual and powered systems. The holding device can have a plurality of holding arms, of which only some, or all, are each connected to a surgical instrument via a docking device according to the invention.

In a further embodiment, the surgical holding device is a surgical robot with a robot head. A surgical robot in this case can be a holding device which has a control device for moving the holding arm in a controlled manner; the robot head forms the end of the holding arm, on which an end effector, to which the movements of the kinematics are to be transferred, can be connected. The holding arm can be controlled remotely; in this case, the control device comprises at least one operating element via which operator inputs are captured; or, it runs completely automatically via a corresponding programming stored in the control device.

According to a further embodiment of the surgical holding device according to the invention, the control device is connected to a first laser device and a second laser device. The laser devices are aligned with each other in such a way that the laser beams emitted by them intersect at a predetermined intersection point. In a preferred embodiment, therefore, the first laser device is arranged at the first opening of the first adapter and the second laser device is arranged at the second opening of the first adapter of the docking device, such that the beam direction results from the inclination of the openings. The two laser beams can have two different colors for better differentiation. Each of the laser devices in this case can be a laser fiber which can be connected to a laser beam source, or a laser module with its own laser beam source.

Controllable in this case means that there is an operative connection between the laser devices and the control device, such that, for example, the laser devices can be activated and deactivated by the control device. For this purpose, a docking program can be stored in the control device, via which movements of the holding arm can be carried out during the connection process, or the manual movement of the same can be allowed or blocked.

The surgical robot can be arranged on a mobile base and thus freely positioned in space.

A method according to the invention for connecting a holding arm of a surgical holding device, in a docking situation, by means of a docking device according to the invention, having a surgical instrument which has a rod-shaped shaft and a handle and is designed to be guided via a trocar, comprises the following steps:
a) connecting the first adapter to the holding arm,
b) arranging the second adapter on the surgical instrument,
c) guiding the second adapter to the first adapter by moving the surgical instrument, and connecting the second adapter to the first adapter by bringing the terminal connection surface of the first engagement element of the first adapter into engagement with the first corresponding engagement element of the second adapter, thereby connecting as a whole the holding arm with the surgical instrument.

As a result, the connection can be established in the simplest manner, by means of which connection the holding of the surgical instrument is made possible, which instrument is directly positioned with a certain penetration depth (depending on the length of the shaft) and inclined at the predetermined first angle. It does not matter in which order steps a) and b) are carried out, as long as they take place before step c).

In a further refinement of the method according to the invention, the following steps are carried out after step b) but before step c):
b1) positioning the surgical instrument by inserting the shaft into the trocar, which is pivotably mounted about a predetermined/fixed pivot point,
b2) by means of the laser device arranged at the first opening, emitting a first laser beam in a predetermined direction and aligning the first laser beam to the pivot point by moving the holding arm and thus the first adapter,
b3) by means of the second laser device arranged at the second opening of the first adapter, emitting a second laser beam in a predetermined direction, which intersects the first laser beam at a predetermined intersection point, and aligning the second laser beam on the pivot point by moving the holding arm parallel to the first laser beam, thereby aligning the first adapter and consequently the holding arm with the pivot point, Step a) can optionally also be carried out only after step b1), wherein the remaining steps are preferably carried out in the order shown.

This corresponds to the usual workflow in a microsurgical procedure assisted by holding devices, in which the instrument is first inserted into a trocar and its pivot point is thus fixed before it is attached to a holding arm. The pivot point is specified by the localization of the trocar, wherein it is possible for the surgical instrument to pivot or tilt around the pivot point where the trocar is also pivoted or tilted.

Steps a) to b1) are carried out manually, whereas the holding arm can be moved in steps b2) and b3) manually or by electronic control. When the second laser beam is aligned with the pivot point in step b3), the alignment of the first laser beam with the pivot point is maintained by the holding arm—which is already connected to the first adapter—being moved only parallel to the first laser beam, i.e., in the direction in which the laser beam travels. After that, the position of the holding arm with the first adapter is no longer changed. Thus, in step c) the point of intersection of the laser beams lies in the pivot point and thus at the same time at a prespecified distance from the holding arm and from the first adapter. The surgical instrument, which is now connected and pre-positioned, can be repositioned, proceeding therefrom, via movements transmitted by the holding arm.

After the holding arm is connected to the surgical instrument, the laser beams can be switched off again.

The method according to the invention can furthermore comprise step a0) before step a)—specifically, attaching a flange piece of the docking device to the holding arm or to a counter-flange attached to it, such that the first adapter does not have to be connected directly to the holding arm, wherein the connection is made by engagement in the flange piece.

In a further embodiment, when the first adapter is connected in step a) to the tip of the first adapter, a sterile drape surrounding at least the holding arm can be pierced, such that contacting—including electrically—is possible while maintaining a sterile operating space. Furthermore, such a drape can also be clamped between the holding arm or the flange piece arranged thereon and the first adapter.

In a further embodiment of the method, the surgical instrument is connected to a holding arm of a surgical robot according to the invention by means of a control device.

The following steps are then preferably carried out:
  b2'), after step b2), in the control device, blocking movements of the holding arm that are not parallel to the first laser beam,
  b3'), after step e), registering the pivot point by registering the intersection of the first and second laser beams in the control device, and storing the registered pivot point in the control device in order to carry out controlled movements of the holding arm with respect to the registered pivot point.

The pivot point with which the holding arm is aligned is advantageously stored in the control device by step b3'), such that the surgical robot receives a reference point with respect to an external body and can consequently coordinate movements around it. The external body can be a patient body for a surgical procedure. Thanks to the precise pre-positioning, the registered pivot point corresponds to the target pivot point, thus reducing damage to the patient's tissue. A minor system-inherent error due to the fact that the first laser beam does not exactly depict the extension of the instrument shaft, but rather runs with an offset to it—albeit a small one—can be compensated for by calculation.

The optional step b2') simplifies the movement of the holding arm parallel to the first laser beam and ensures that the alignment of the first laser beam with the pivot point is maintained in the further steps

BRIEF DESCRIPTION OF THE DRAWING

These and further embodiments of the docking device and the method, as well as some of the advantages associated with these and further embodiments, will be made clearer and more understandable from the following detailed description with reference to the accompanying drawings. Objects or parts thereof that are substantially the same or similar can be provided with the same reference signs. The drawings are only a schematic representation of an embodiment of the invention.

In the drawings.

DETAILED DESCRIPTION

The invention comprises a docking device having a two-part adapter device, wherein the first adapter can be connected directly or via a flange piece of the docking device to a holding arm of a surgical holding device, and the second adapter can be connected to a surgical instrument, such that the surgical instrument is held by the holding arm when the first and second adapters are engaged with each other. The invention also relates to a surgical holding device which is connected to a surgical instrument via the docking device, and to a method for connecting the surgical instrument to the holding arm by means of the docking device according to the invention. The holding arm can be part of a surgical robot.

FIGS. 1 to 10 show an embodiment of the docking device 1 according to the invention in various connected and disconnected states of the individual parts. The holding arm of the holding device to which the docking device 1 docks the surgical instrument 2 is not shown in the figures. The screw connections 17 via which each mating flange 16 is attached to the holding arm, wherein the same disappear, in practice, of course in corresponding bores or other connection points of the holding arm or robot head, if it is the holding arm of a surgical robot, can be seen instead.

Figure 1:
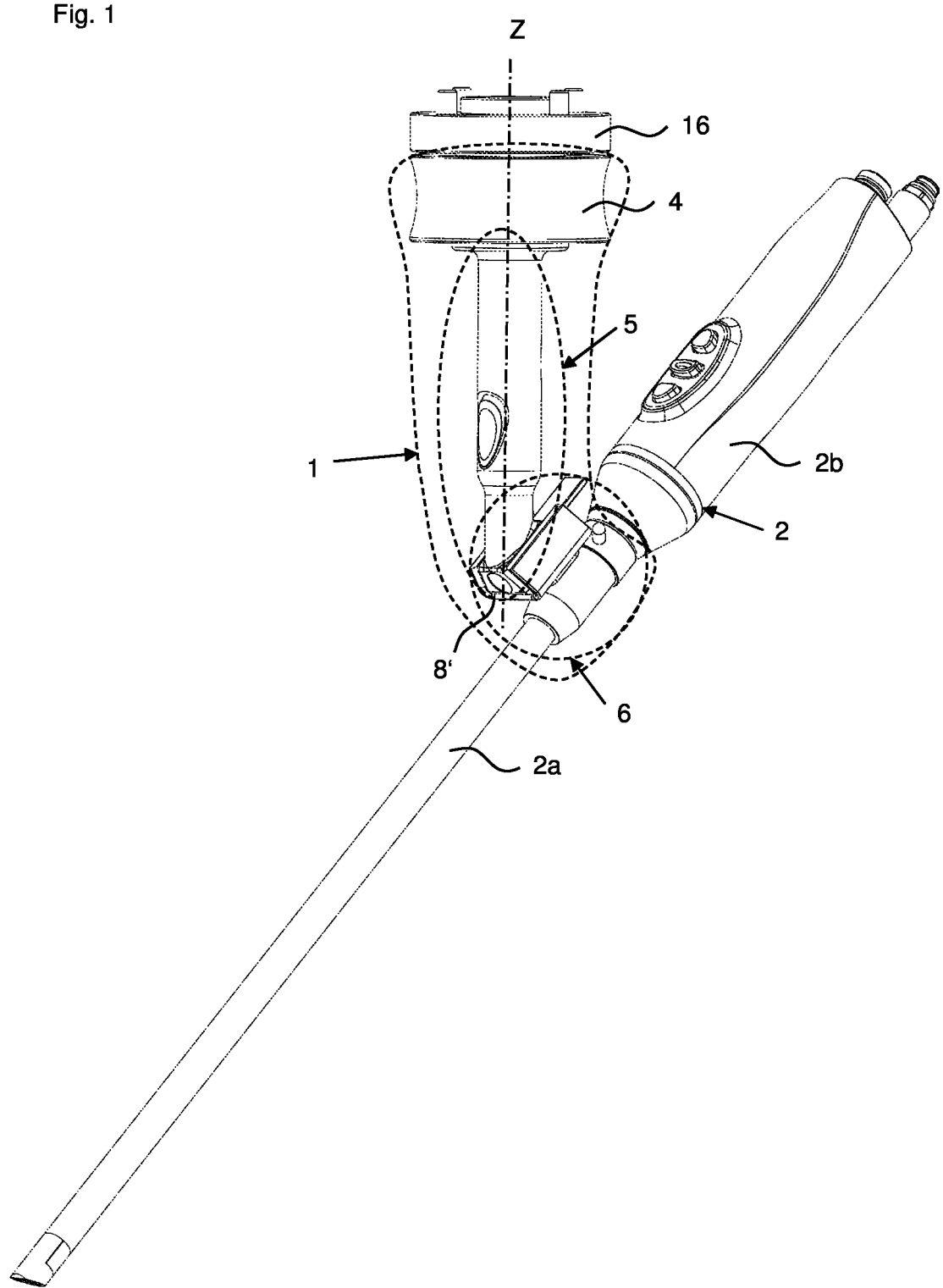
FIG. 1 is a perspective view of the docking device, connected to a mating flange of a holding arm and to a surgical instrument.

FIG. 1 shows (without showing the holding arm) the docking device 1 in the completely connected state, connected at a proximal end to the mating flange 16 of a holding arm via a flange piece 4, and connected to a surgical instrument 2 at a distal end. The first adapter 5 is connected to the flange piece 4 and to the second adapter 6. In this state, the surgical instrument 2 is therefore ready to be held by the holding arm and optionally also to be repositioned.

The surgical instrument 2 which will be coupled to the holding arm with the docking device 1 has an elongated shaft 2a which is connected at its proximal end to a handle 2b; at its distal end, a tool (not shown) such as a manipulator or a camera (endoscope) can also be present. The corresponding connections for mechanical and/or electrical contacting and handling of the tool with the handle 2b run via the shaft 2a.

Figure 2:
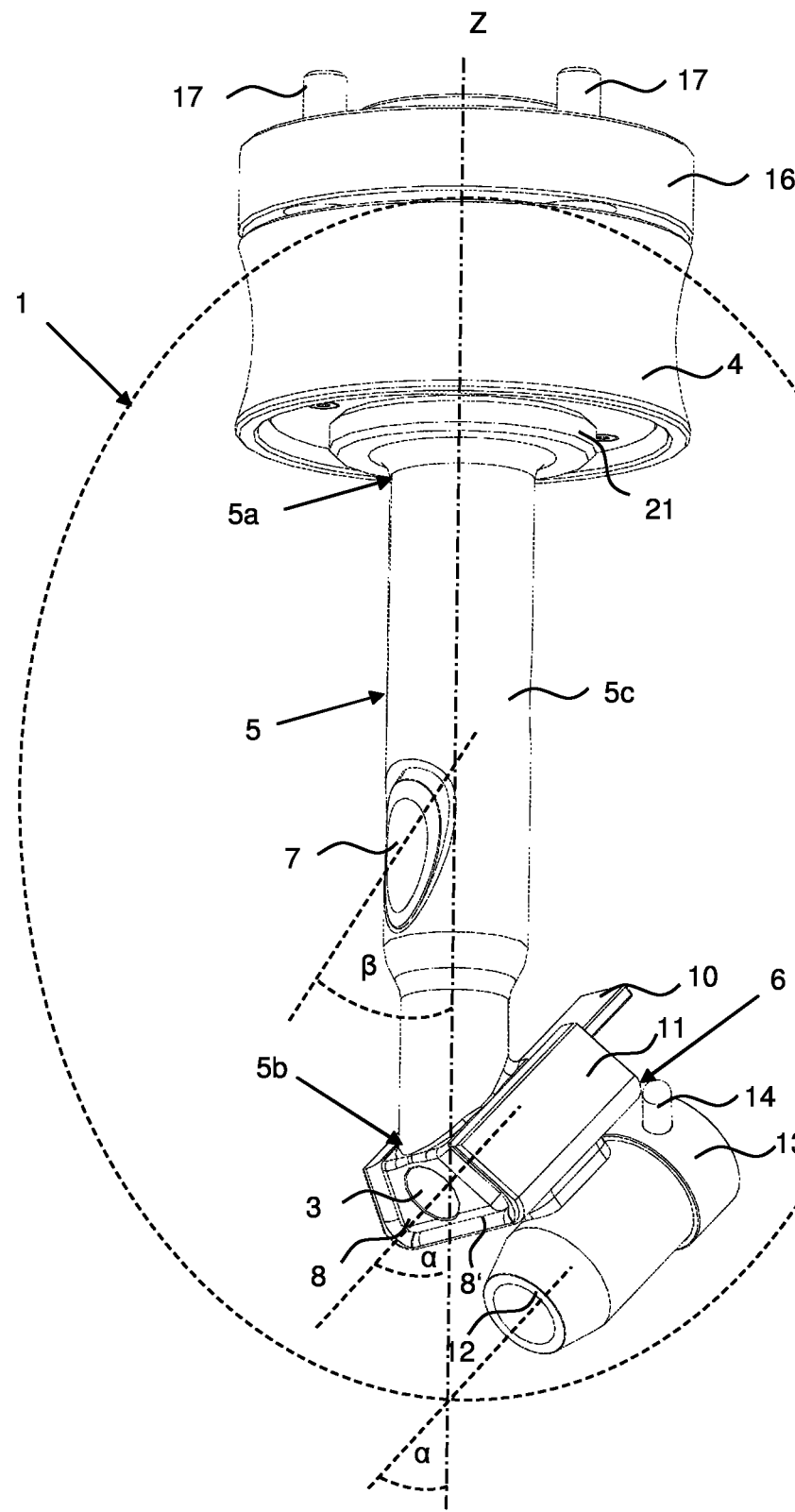
FIG. 2 is a perspective view of the docking device, connected to a mating flange of a holding arm.

In FIG. 2, the docking device 1 is shown without a surgical instrument 2 for the sake of clarity, although the first adapter 5 is nevertheless connected to the second adapter 6—a state that is usually not established since the second adapter 6 is always connected to the surgical instrument 2 before it docks to the first adapter 5.

Figure 5:
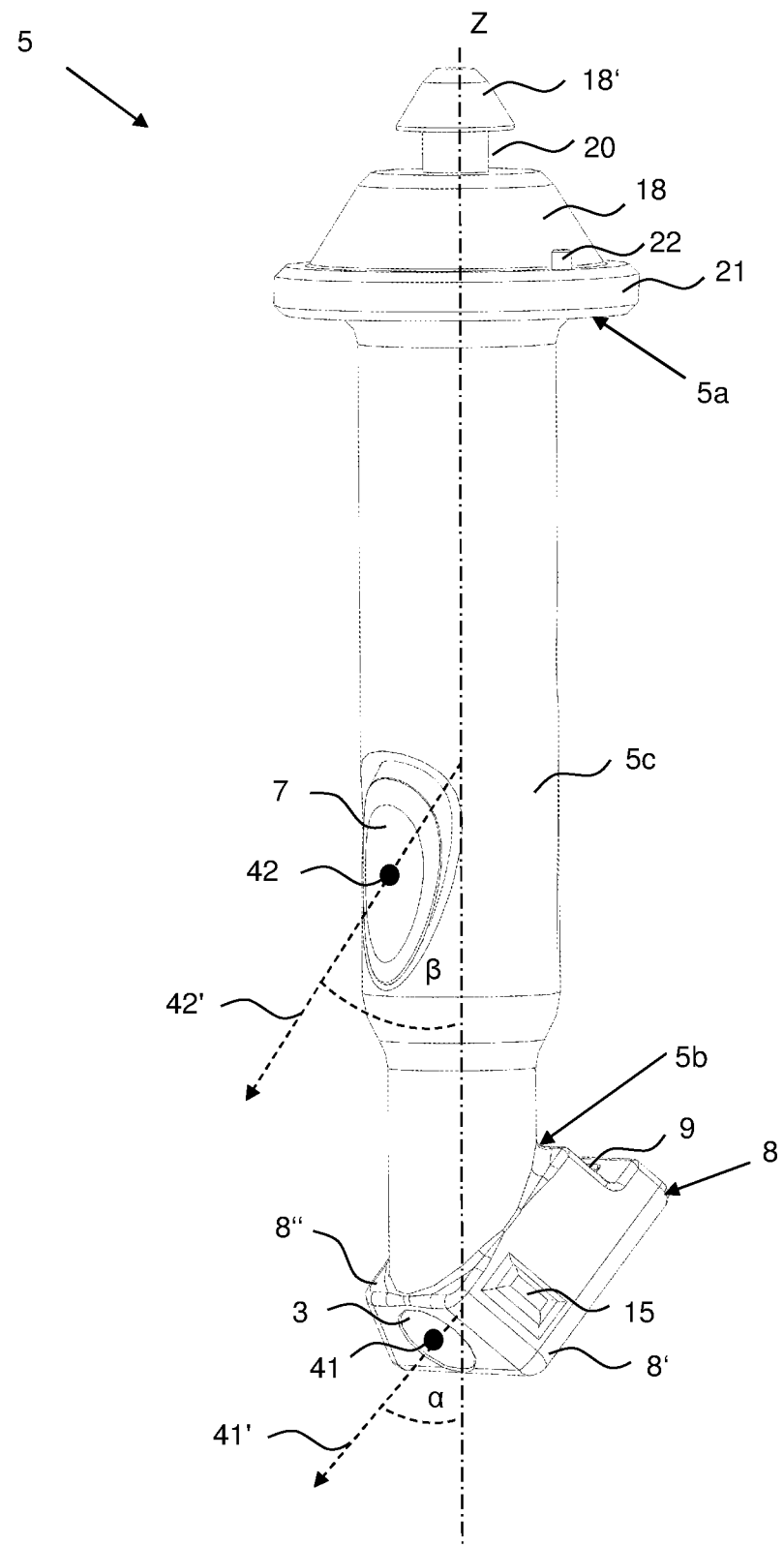
FIG. 5 is a perspective view of the first adapter.
Figure 6:
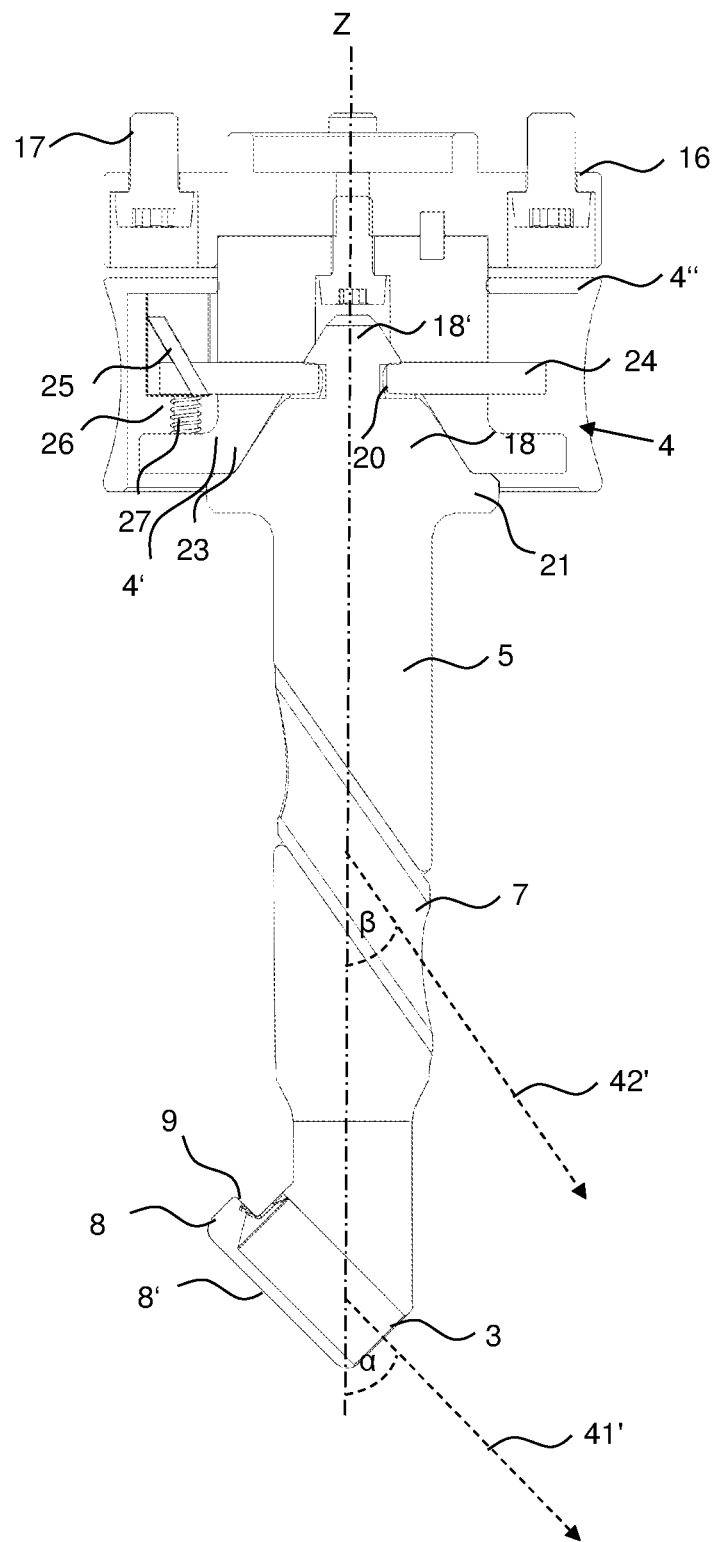
FIG. 6 is a longitudinal sectional view through the first adapter and the flange piece of the docking device, connected to the mating flange of the holding arm.

In FIG. 2, the docking device 1 is shown connected to a flange piece 4 specially designed for receiving the holding cone 18—which is shown in FIGS. 5 and 6—of the first adapter 5. This flange piece 4 is attached in a simple manner, for example by screw connections 17, to the corresponding (standard) connections of a mating flange 16 of the holding arm, such that the flange piece 4 furnishes the corresponding engagement element—which in the embodiments shown is the recess 23—for the proximal end 5a of the first adapter 5.

The holding arm can, however, also have a standardized flange (these are known in particular for various surgical robot systems and are present on the robot head of the given holding arm) on which there is an engagement element of the holding arm that corresponds to a suitably designed first engagement element of the first adapter, such that the first adapter can be coupled directly.

As shown in FIGS. 2, 3, 4 and 5, the first adapter 5 has a proximal end 5a for connection to the holding arm and a distal end 5b for connection to the second adapter 6, and an elongated section 5c therebetween. At the distal end 5b there is a connecting body 8 which widens from a side 8" facing the elongated portion 5c to a terminal connection surface 8', and thus forms a type of slide or dovetail with a trapezoidal or dovetailed cross-section. A first engagement element of the first adapter 5 is thus provided by the connecting body 8. Alternative embodiments not shown can provide the first engagement element as a part of the connecting body or an element arranged thereon. The connecting body 8 fits with its connection surface 8' into a corresponding engagement element 11 on the second adapter 6, which in this case is a slide mount in the form of a rail element 11.

It is conceivable that the mutually corresponding elements are interchanged—that is to say, the first adapter 5 has a rail element and the second adapter 6 has a slide. It goes without saying that the connection mechanisms shown are only examples of other engagement elements that correspond to each other.

The first adapter 5 also comprises a longitudinal axis Z of the elongated portion 5c, which after coupling to the holding arm (at a 90° angle to its end face) can run vertically as shown. This corresponds to a coupling situation that is often encountered, but it can also deviate from the vertical. When connecting the first adapter 5 to the holding arm, a clear orientation of this longitudinal axis Z is thus established.

The entire connecting body 8 and thus in particular its terminal connection surface 8' is angled by the angle $\alpha$ with respect to the longitudinal axis Z of the elongated portion 5c, such that the connection with the second adapter 6 takes place at precisely this angle. As a result, a fixed connection angle is ultimately established between the surgical instrument 2 and the holding arm. Docking devices 1 with different angles can be provided. For the docking situation shown, an angle in a range from 30° to 90°, preferably in a range from 45° to 75°, in particular around 60° or 45°, has proven to be useful, thereby bringing the surgical instrument 2 into a normal position for use in a laparoscopic procedure.

Figure 3:
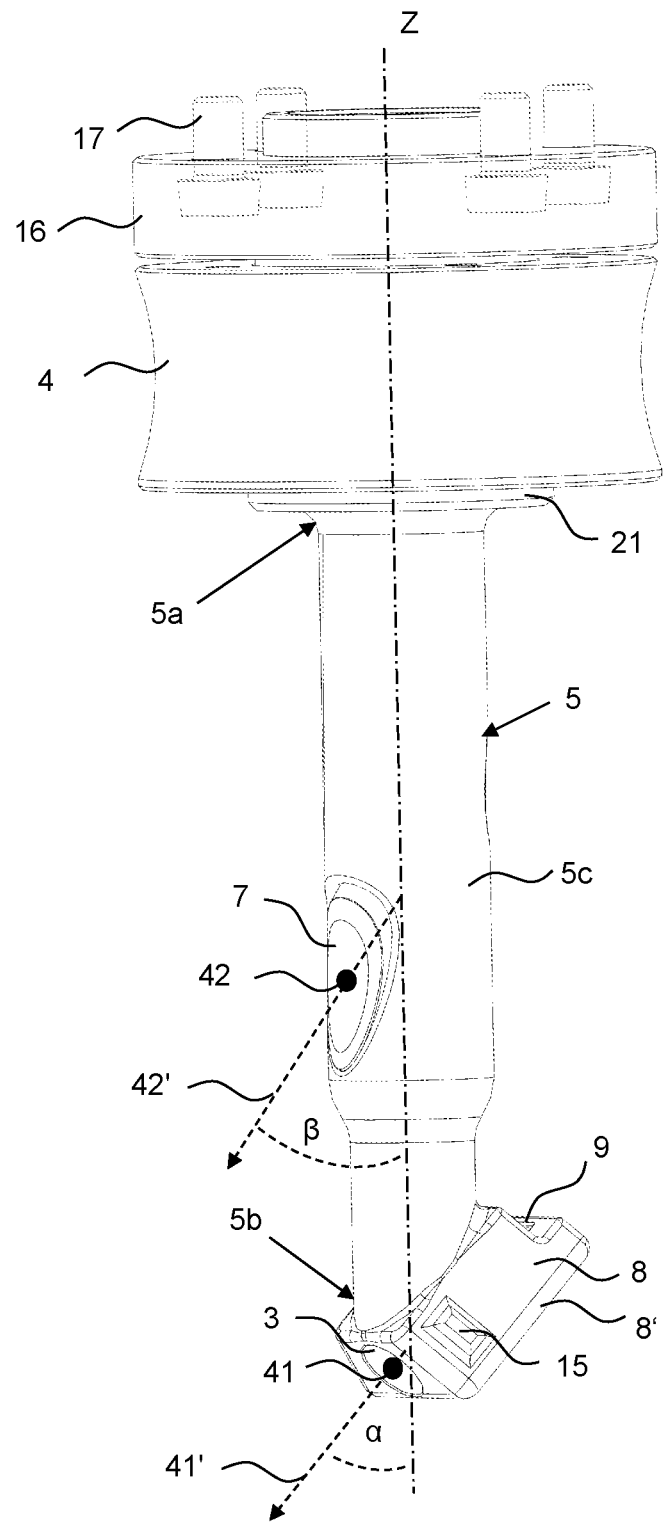
FIG. 3 is a perspective view of the first adapter and the flange piece of the docking device, connected to a mating flange of a holding arm.

In FIGS. 2, 3 and 5, the connecting body 8 of the first adapter 5 shows a first opening 3 for the exit of a first laser beam 41'. A first laser device 41, for example in the form of a laser fiber (shown as a point in FIGS. 3 and 5) is integrated into the connecting body 8 at the first opening 3. The first opening 3 can be closed by a transparent window, which is not shown in the figures. The first opening 3 is inclined at a first angle $\alpha$, the first opening 3 being shown in FIGS. 2, 3 and 5 as a through-opening with beveled edges. For better understanding, in FIGS. 3 and 5 the laser beam 41' is drawn back with dashed lines up to the longitudinal axis Z in order to show the angle $\alpha$. The laser beam 41' radiates away from the first adapter 5 along the angle of inclination of the first opening 3 in a direction angled by the first angle $\alpha$ relative to the longitudinal axis Z, i.e., parallel to the terminal connection surface 8' and parallel to the connecting direction between the connecting body 8 of the first adapter 5 and the rail element 11 of the second adapter 6. In its elongated portion 5c, the first adapter 5 has a second opening 7 for a second laser device 42—as just described for the first laser device 41—which emits a second laser beam 42'. The second opening 7, like the first opening 3, is shown in the figures as a through-opening. In order to represent the angle $\beta$ in FIGS. 3 and 5, the second laser beam 42' is likewise extended to the longitudinal axis Z of the adapter 5 with dashed lines. The second laser beam 42' radiates away from the first adapter 5 in the direction of inclination of the second opening 7 in a direction angled by the second angle $\beta$ with respect to the longitudinal axis Z, the second angle $\beta$ being smaller than the first angle $\alpha$. The second laser beam 42' runs in the plane that is defined by the longitudinal axis Z and the first laser beam 41', and intersects the first laser beam 41' at a predetermined intersection point 44. The function thereof is described in more detail in connection with FIG. 11a to 11g.

From the sectional view in FIG. 6, in which the openings 3, 7 are through-openings, it can be seen that in this case the direction of the laser beams 41', 42' results from the alignment of the openings 3, 7.

Figure 4:
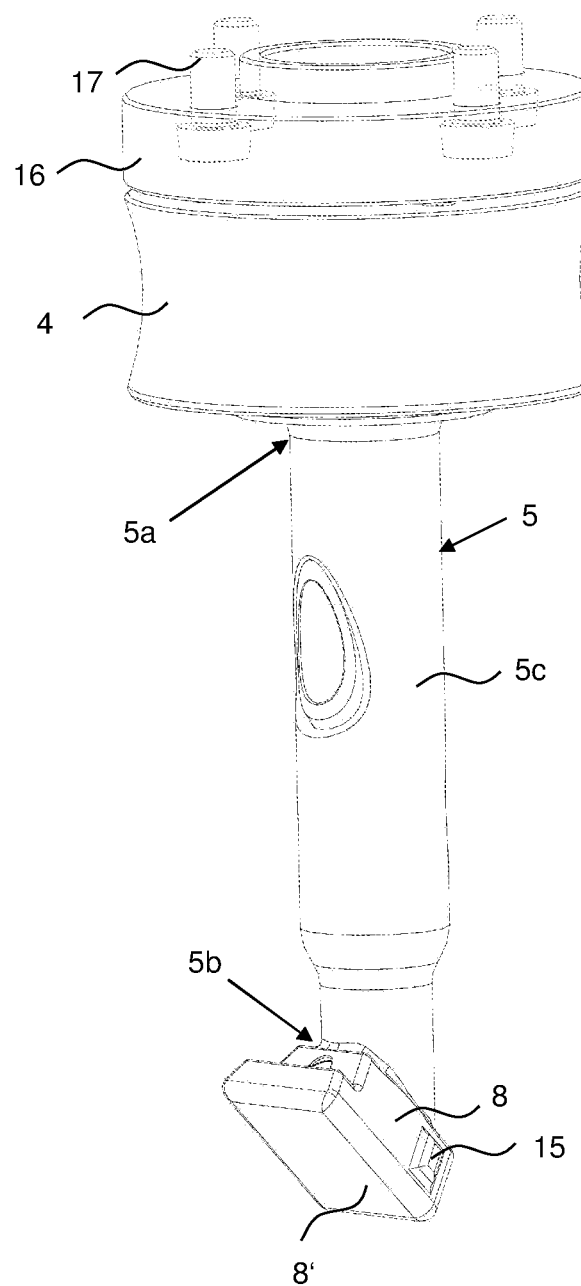
FIG. 4 is a further perspective view of the first adapter and the flange piece of the docking device, connected to a mating flange of a holding arm.

FIGS. 3 and 4 show the first adapter 5 as it should be present for the releasable connection to the second adapter 6, namely already connected to the flange piece 4 and ready to be connected via the connecting body 8 on which the first engagement element is present, or which itself forms the first engagement element to be brought into engagement with the rail element 11 of the second adapter 6.

In FIGS. 5 and 6, the holding cone 18 is formed as a second engagement element at the proximal end 5a of the first adapter 5, and tapers from the elongated portion 5c into a tip 18'. On its broad side, the holding cone 18 is limited by a circumferentially protruding collar 21. The holding cone 18 is used to connect to a flange piece 4 attached to the mating flange 16 of the holding arm, the conical recess 23 of which can receive the holding cone 18. The holding cone 18 has a recess in the form of a circumferential annular groove 20.

The connection to a flange piece 4 specially designed for the adapter device 1 is shown in the sectional view in FIG. 6. The flange piece 4 has a flange body 4' connected, for example screwed, to the mating flange 16. The conical recess 23 which corresponds to the shape of the holding cone 18 is present in the flange body 4'. One or more movably mounted holding rails 24 protrude into the recess 23 and are guided via a guide 25. If the holding cone 18 of the first adapter 5 is inserted into the recess 23, the holding rail 24 is pushed outward from the tip 18' and a sleeve 4" which is movable relative to the flange body 4' is pushed down. When the holding cone 18 has been pushed in so far that the annular groove 20 is level with the holding rail 24, the holding rail 24 can move inward again, and thus locks the holding cone 18 and consequently the first adapter 5 on the flange piece 4. A spring 26 guided by a pin 27 resets the sleeve 4" and the holding rail 24. To release the first adapter 5, the reverse procedure can be used—that is, by engaging the sleeve 4", the holding rail 24 is forced out of the annular groove 20 and the path of the holding cone 18 out of the recess 23 is made free.

Furthermore, an alignment pin 22 which points in the direction of the tip 18' is arranged on the protruding collar 21. This will be inserted into a pin-shaped recess on the flange piece 4 (also not visible in the sectional view), such that the first adapter 5 can only be connected in a clear alignment with respect to the flange piece 4 and thus the holding arm. These or comparable alignment aids for clear alignment are optional and further simplify the connection process.

The holding arm and the flange piece 4, if this is to be used as part of the docking device 1, can be wrapped in a sterile drape (disposable cover) for a sterile operation setting. So that the first adapter 5 can still be coupled without any problems, the tip 18' of the holding cone 18 can pierce the drape when it is inserted into the conical recess 23, such that the path to the flange is cleared. The tip 18' is nevertheless slightly rounded in order to avoid injuries to the medical staff during handling. Thus, not only is a purely mechanical connection possible, but electrical contact points can also be present in the holding cone 18, which are then contacted accordingly by parts of the holding arm and ensure an electrical or electronic coupling. These can be, for example, power supply lines for the laser devices 41, 42. The section of the drape around the holding cone 18 of the first adapter 5 can also be received in a narrow gap that remains between the first adapter 5 and the flange piece 4. The remaining parts of the docking device 1, in particular the first and second adapters 5, 6, are located in the sterile space and must therefore themselves be sterile. The docking device 1 is therefore designed as a single-use product, which is disposed of after use, or as a sterilizable reusable product, wherein at least the two-part adapter device can be sterilized.

Figure 7:
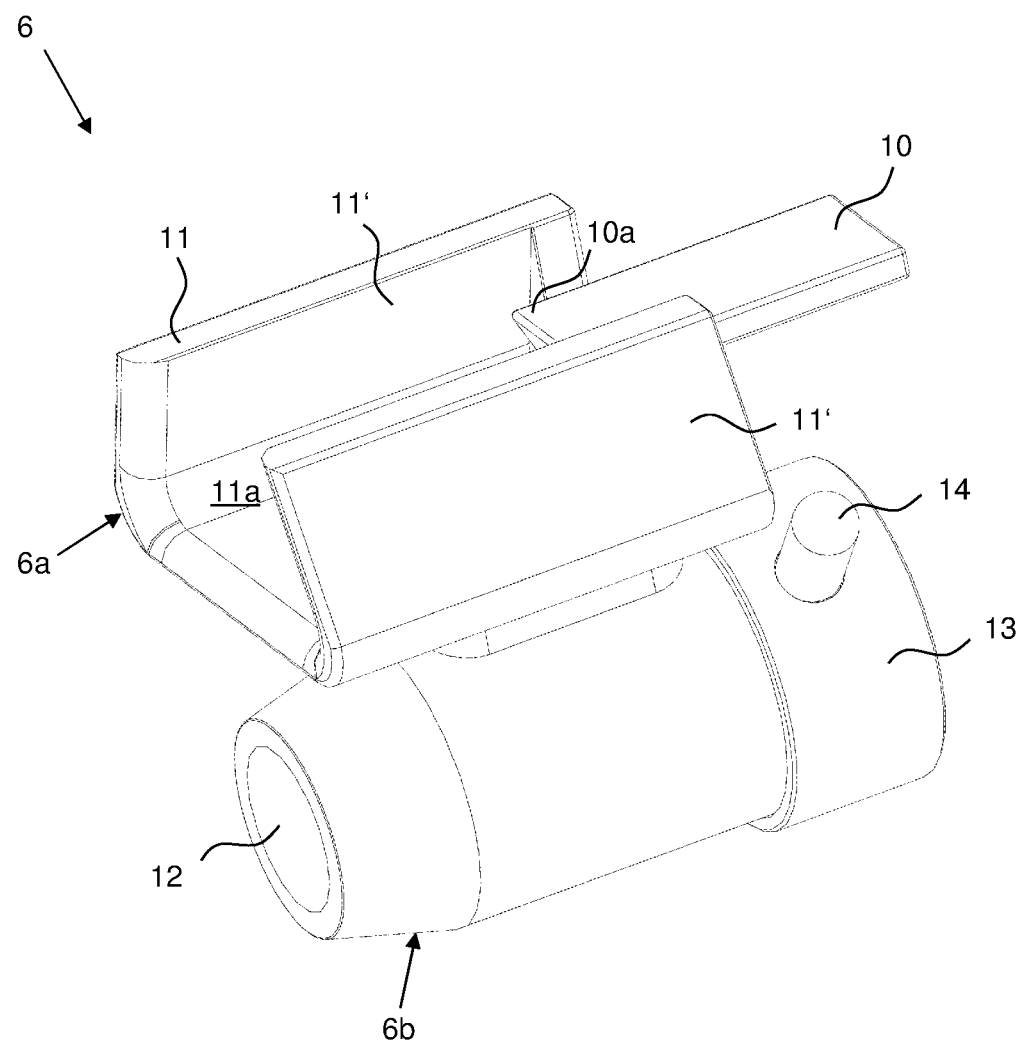
FIG. 7 is a detailed view of the second adapter.
Figure 8:
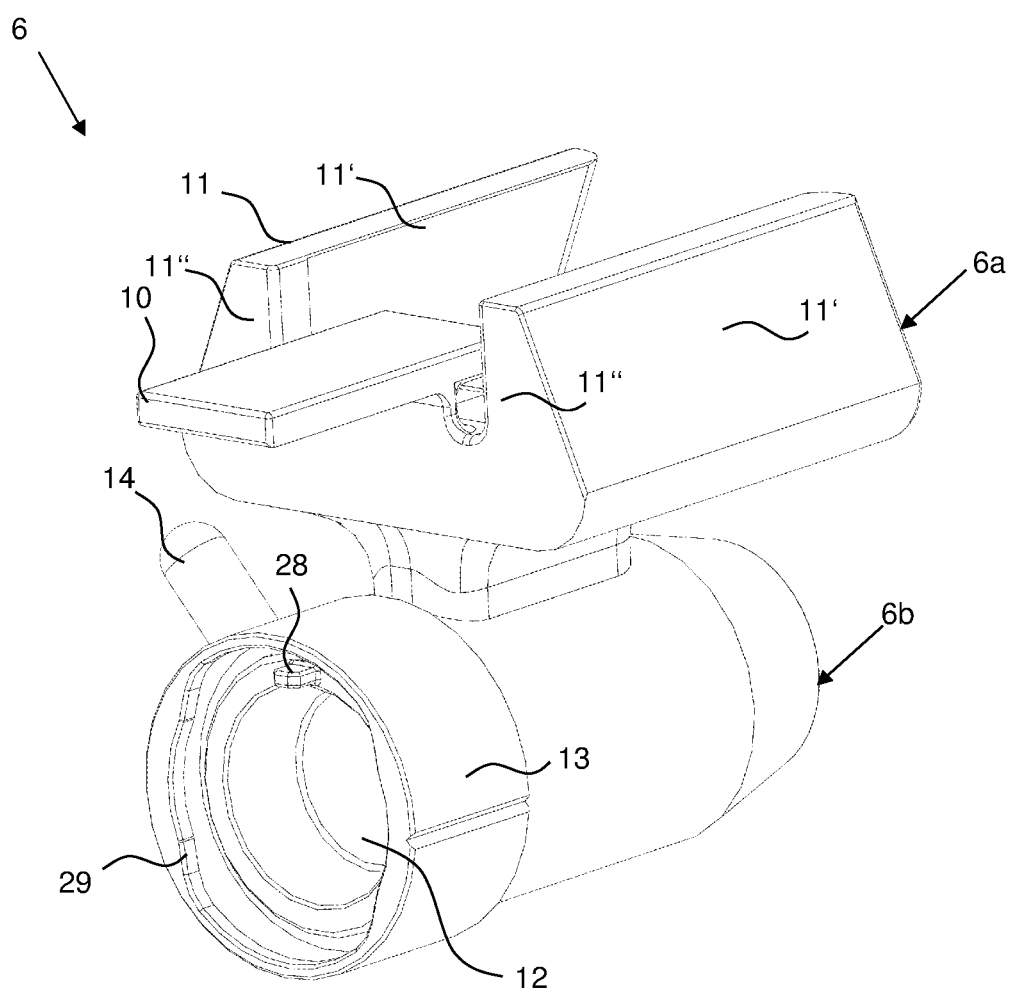
FIG. 8 is a further detailed view of the second adapter.
Figure 9:
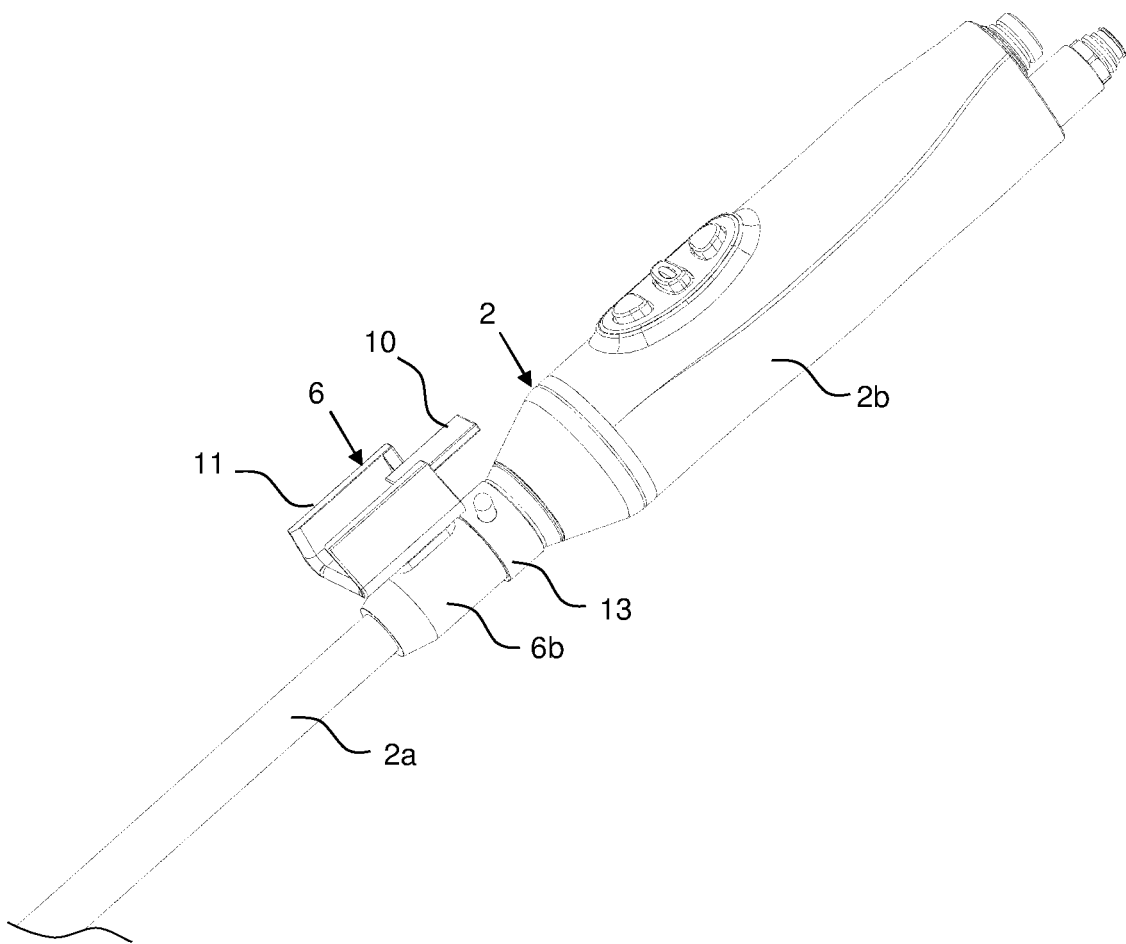
FIG. 9 is the second adapter, arranged on a surgical instrument.

FIGS. 7 and 8 show that the second adapter 6 has a rail section 6a and a tubular portion 6b. On the rail section 6a there is a rail element 11 which, in the docking situation, points upwards—that is, to the terminal connection surface 8' of the connecting body 8 of the first adapter 5, and is open on this side. The tubular portion 6b adjoins the closed, lower side. The rail element 11 corresponds to the terminal connection surface 8' in such a way that it forms a receiving space 11a for the connecting body 8 of the first adapter 5. For this purpose, the side walls 11' of the rail element 11 diverge towards the tubular portion 6b of the second adapter 6, such that the rail element 11 has a trapezoidal or dovetail-shaped contour. Thus, the adapters 5, 6 can only be connected to each other along a longitudinal axis of the rail element 11. For this purpose, the connecting body 8 is pushed from a longitudinal end of the rail element 11 into the receiving space 11a, such that the first adapter 5 and the second adapter 6 are clearly aligned with each other. A connection that is rotated by 180° is not possible because only one longitudinal end of the rail element 11 is exposed in order to insert the first adapter when the second adapter 6 is already arranged on the surgical instrument 2. In addition, the side walls 11' can diverge towards this exposed longitudinal end in order to facilitate insertion. On a second longitudinal end of the rail element 11, it is delimited by rear walls 11", such that the slide 8 does not slide through. The connection is released simply by sliding it lengthways in the opposite direction.

On the second longitudinal end of the rail element 11, there is a securing clip 10 with a nose 10a facing the receiving space 11a, which can engage in a corresponding notch 9 on the connecting body 8 of the first adapter 5 to secure against unintentional loosening. In order to release the securing device, pressure can be exerted on the securing clip 10, which then bends open so that the nose 10a is lifted out of the notch 9. On the connecting body 8 of the first adapter 5 there can be securing projections 15 which can additionally ensure a firm hold within the rail element 11.

Figure 10:
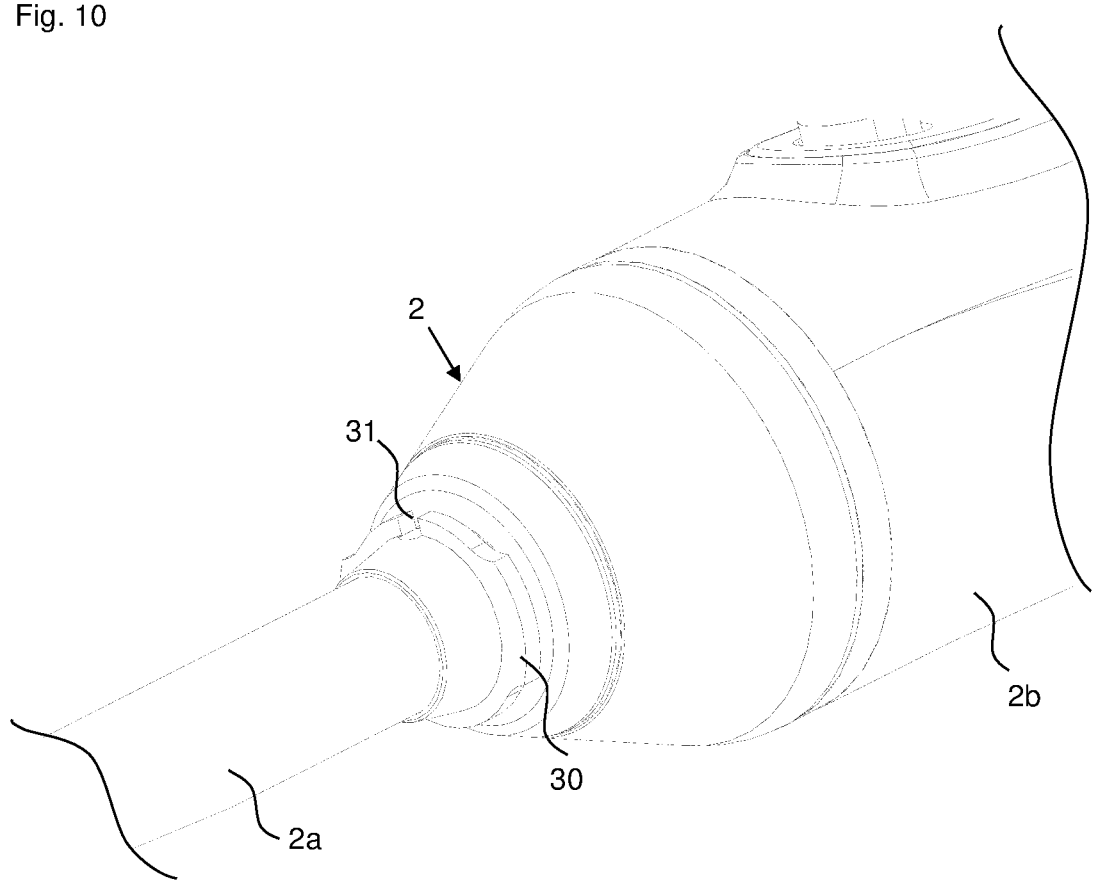
FIG. 10 is a detailed partial view of the proximal end of a shaft of a surgical instrument to which the second adapter of the docking device can be attached.

The rail section 6a is followed by a tubular portion 6b which has a through-opening 12 which runs parallel to the rail element 11, more precisely parallel to its longitudinal axis, along which the two adapters 5, 6 are connected to each other. FIG. 8 shows that a coupling element 13 in the form of a connecting ring with a gripping nipple 14 is provided at the distal end of the tubular portion 6b, the connecting ring 13 having a shaped recess 29 on the circumferential inside, as well as an alignment pin 28. The connecting ring 13 is rotatable, the gripping nipple 14 facilitating the rotation of the connecting ring 13 in order to couple the adapter to the endoscope. The gripping nipple 14 can also have a pin in order to facilitate the guidance of the coupling inside the connecting ring 13 and to limit the radius of rotation of the connecting ring 13. In order to connect the second adapter 6 to the surgical instrument 2 in the arrangement shown in FIG. 9, the shaft 2a of the surgical instrument 2 is pushed through the passage opening 12 starting from its distal end, until the coupling element 13 of the second adapter 6 abuts the handle 2b of the surgical instrument 2. There are further connecting elements on the instrument 2, as also shown in FIG. 10, namely a corresponding coupling element 30 which protrudes in a manner corresponding to the shaped recess 29, such that they interlock when the coupling element 13 is, as it were, slipped over during coupling. The adapter 6 cannot slip past the handle 2b. Furthermore, the alignment of the second adapter 6 on the surgical instrument 2 is clearly defined by the groove 31 on the projection 30, into which the alignment pin 28 must be inserted when it is slipped over. The alignment can also already be determined by the shaped recess 29 and the projection 30 alone, and the alignment pin 28 may not be necessary. The shaped recess 29 and the projection 30 are preferably rotationally symmetrical to each other by 180°; the combination of the alignment pin 28 and the groove 31 determines the alignment, as shown in FIG. 10 in conjunction with FIG. 8. Decoupling takes place analogously by pushing the tubular portion 6b back over the shaft 2a.

Alternatively, it is conceivable that the second adapter is pushed, bent or otherwise connected laterally over the shaft, for example with Velcro® brand hook and loop tape or adhesive tape. Another position of the second adapter on the shaft, and/or also partially pushed over the handle, is alternatively possible. It should only be noted that the corresponding engagement element of the second adapter is then present in such a way that it can be connected to the second engagement element in the intended orientation and thus also specifies the direction of the shaft.

FIGS. 11a to 11g show relevant steps of the method according to the invention for connecting the surgical instrument 2 to the holding arm, both the holding arm and the instrument 2 being pre-positioned so that a low-stress connection and a sensible starting position for a subsequent surgical procedure are possible. The prepositioning can be assisted via the control device of the holding arm in order to further facilitate the method for connecting the surgical instrument 2 to the holding arm.

Each of the movements are carried out in the direction of the block arrow (and also in a third dimension outside the plane of the drawing). In a) and b), the surgical instrument is not yet fixed in a pivot point 43 with respect to a body 45, so the movements have no influence on the body 45 and can therefore be carried out essentially freely. Starting from the docking situation shown in FIG. 11c, the surgical instrument 2 may only be moved around a fixed pivot point 43 with respect to the body 45; for this reason, the holding arm and the first adapter 5 are moved in steps c) to e), and only in f) to g) are the surgical instrument 2 and the second adapter 6 moved.

Figure 11A:
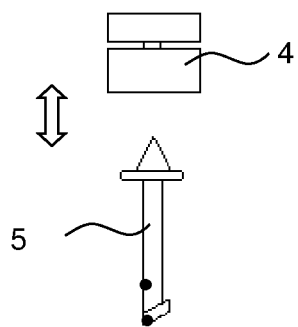
FIGS. 11a-11g show, in a) to g), several intermediate steps in connecting a surgical instrument to a holding arm by means of the docking device.

In FIG. 11a, the first adapter 5 is connected to the holding arm via the flange piece 4. For this purpose, the holding cone 18 is inserted into the recess 23 of the flange piece 4 and secured by engaging the holding rail 24 in the annular groove 22 of the holding cone 18. Alternatively, a second engagement element of the first adapter 5 can be connected directly to a corresponding engagement element of the holding arm—that is to say, without a flange piece 4.

Figure 11B:
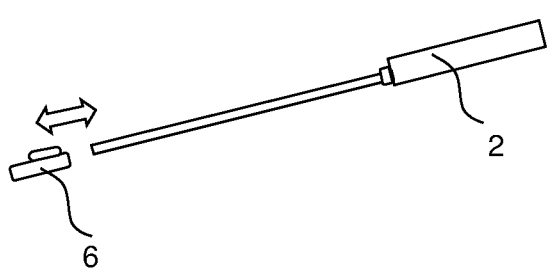

FIG. 11b shows the arrangement of the second adapter 6 on the surgical instrument 2, which can be achieved by inserting the shaft 2a of the surgical instrument 2 into the through-opening 12 of the tubular portion 6b of the second adapter 6 and coupling the coupling element 13 to the corresponding coupling element 30 at the proximal end of the shaft 2a.

Figure 11C:
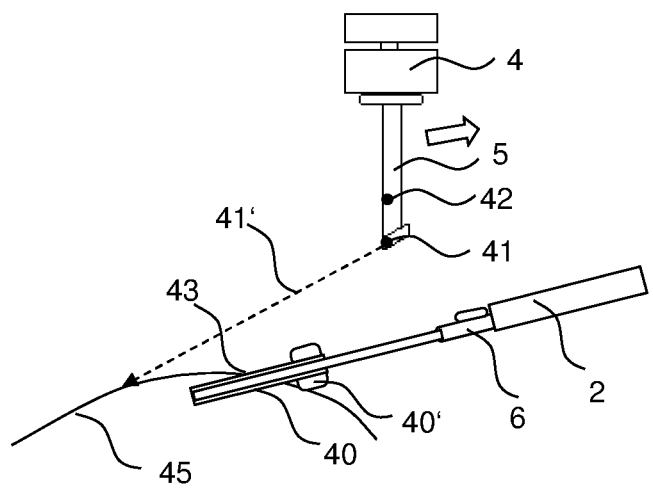

In FIG. 11c, the surgical instrument 2 is placed in a trocar 40 which is mounted in a body 45. The puncture point of the trocar 40 in the surface of the body 45 (for example, the abdominal wall of the patient in a laparoscopic procedure) forms a pivot point 43 with respect to the body 45, around which the instrument 2 (and the trocar 40) is pivoted, wherein the instrument can be moved and rotated along its longitudinal axis without damaging the body 45. However, the pivot point is fixed, insofar as shifting it unnecessarily widens and injures the puncture site.

It is now already possible to guide the two adapters 5, 6 towards each other and to connect them to each other, such that overall the surgical instrument 2 is connected to the holding arm and held by it. Because of the mutually adapted engagement elements of the two adapters 5, 6, this last connection step can be carried out particularly easily and reliably.

Figure 11D:
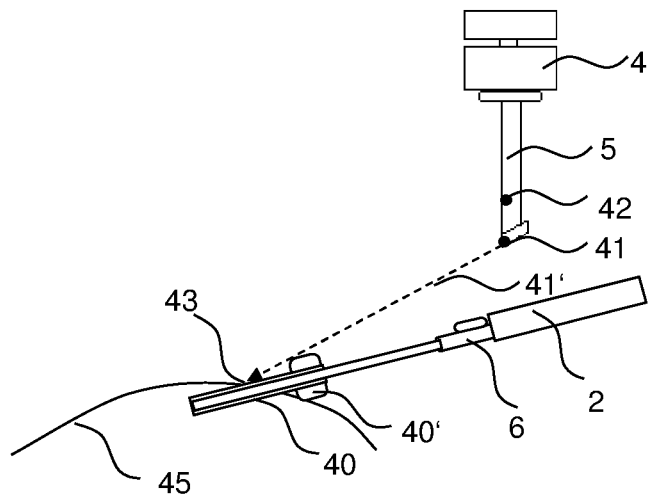

However, the holding arm can particularly advantageously be prepositioned in such a way that the first adapter 5 is brought into an ideal position for the last connecting step, and at the same time the location of the pivot point 43 with respect to the holding arm is known. For this purpose, a first laser device 41, which is already arranged on the first opening 3 of the first adapter 5 or is employed at this moment, is activated, and the first laser beam 41' emitted along the direction specified by the first opening 3 is visible on the surface of the body 45. The holding arm and the first adapter 5 are then positioned in space in such a way that the first laser beam 41' runs through the pivot point 43, as FIG. 11d shows. For this, it may be necessary to tilt the surgical instrument 2 and the trocar 40 slightly so that the trocar head 40' does not block the path of the first laser beam 41'.

Figure 11E:
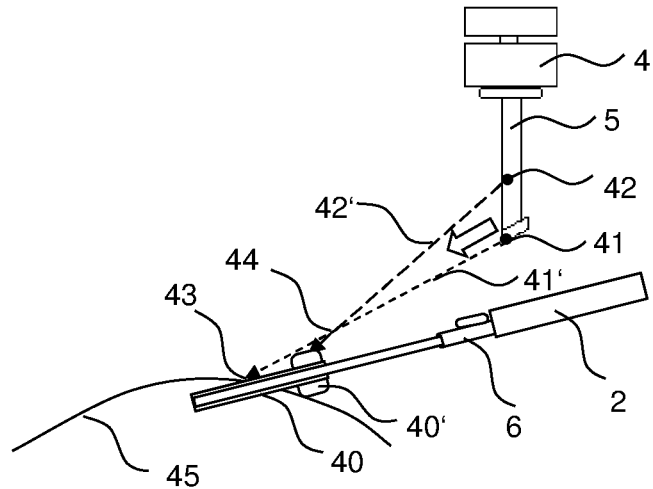
Figure 11F:
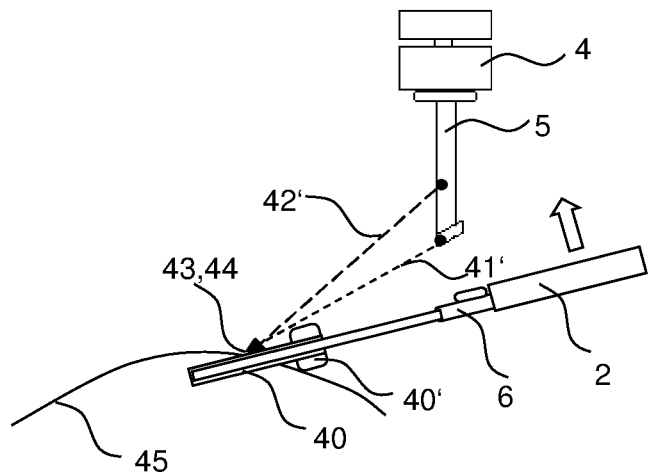

A second laser device 42, which is already arranged on the second opening 7 of the first adapter 5 or is employed at this moment, is then activated, as shown in FIG. 11e. The second laser beam 42' emitted in a predetermined direction intersects the first laser beam 41' at an intersection point 44 predetermined by the angles α, β of the openings 3, 7 with respect to the longitudinal axis Z of the elongated portion 5c and by the distance between the openings 3, 7. In order to place this intersection point 44 on the pivot point 43, the holding arm and the first adapter 5 are moved along the direction of the first laser beam 41', i.e. parallel to it, until the second laser beam 42' also passes through the pivot point 43, which consequently now lies in the intersection point 44 of the laser beams 41', 42', as FIG. 11f shows.

Figure 11G:
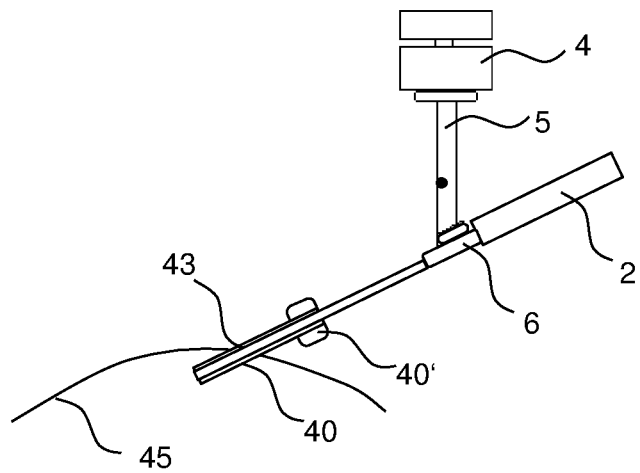

The laser devices 41, 42 can now be deactivated again and the two adapters 5, 6 can be coupled to each other by guiding the surgical instrument 2 with the second adapter 6 to the position of the first adapter 5 on the holding arm, as shown in FIG. 11g, wherein the surgical instrument 2 is pivoted about the fixed pivot point 43. The adapters 5, 6 are brought into engagement in that the surgical instrument 2 is displaced along its longitudinal axis and the connecting body 8 is threaded into the receiving space 11a of the rail element 11. The connection can be secured in that the nose 10a of the securing clip 10 is received in the notch 9 of the connecting body 8.

The pivot point 43 is thus at a point known to the system without having to be specifically placed at this point.

The surgical holding device, to whose at least one holding arm the surgical instrument 2 is docked, can be part of a controllable surgical robot, in whose control device a docking program can be stored so that the described steps can run, supported by the holding device. In response to certain user inputs, for example pressing a button or entering software commands, the laser devices 41, 42 are then activated or deactivated or movements of the holding arm connected to the first adapter 5 are blocked, such that when the intermediate position shown in FIG. 11d/11e is reached, the holding arm can only be moved along an axis parallel to the first beam 41'. This ensures that the previously set position, in which the first laser beam 41' passes through the pivot point 43, is maintained.

The correct positioning of the second laser beam 42' and thus the final docking situation can also be confirmed so that the control device knows and stores the location of the pivot point 43 through the intersection point 44 of the laser beams 41', 42'. As a result, further movements that the surgical instrument 2 will perform, and which will be transmitted by movements of the holding arm, will not displace the pivot point 43.

After the surgical instrument is used, the connections made with the docking device 1 according to the invention can be released again. The flange piece, if one was used, can remain on the mating flange. The two-part adapter device can be disposed of and replaced, or sterilized and prepared for further use.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE SIGNS

1 Docking device
2 Surgical instrument
2a Shaft
2b Handle
3 First opening
4 Flange piece
4' Flange body
4" Sleeve
5 First adapter
5a Proximal end of the first adapter
5b Distal end of the first adapter
5c Elongated portion of the first adapter
6 Second adapter
6a Rail portion of the second adapter
6b Tubular portion of the second adapter
7 Second opening
8 Connecting body
8' Terminal connection surface, end portion 8" Side facing the elongated portion, end portion
9 Notch
10 Safety clip
10a Nose
11 Rail element
11a Receiving space, rail element
11' Sidewall, rail element
11" Rear wall, rail element
12 Through-opening
13 Coupling element, connecting ring
14 Gripping nipple
15 Securing projection
16 Mating flange
17 Screw connection
18 Holding cone
18' Tip, holding cone (pin for piercing)
20 Annular groove
21 Collar
22 Alignment pin, first adapter
23 Recess
24 Holding rail
25 Guide of the holding rail
26 Spring
27 Pin
28 Alignment pin, second adapter
29 Shaped recess
30 Projection
31 Groove
40 Trocar
40' Trocar head
41 First laser device
41' First laser beam
42 Second laser device
42' Second laser beam
43 Pivot point
44 Intersection of the laser beams
45 Body
Z Longitudinal axis
α first angle
β second angle

The invention claimed is:

1. A docking device which is designed to connect a surgical instrument to a holding arm of a surgical holding device in a docking situation, wherein the surgical instrument has a rod-shaped shaft and a handle, and is designed to be guided by a trocar,
characterized in that
the docking device has a two-part adapter device which can be connected at a proximal end to the holding arm and at a distal end to the surgical instrument,
the two-part adapter device having
a first adapter
with an elongated portion which has a longitudinal axis (Z), and
with a connecting body which is present at a distal end of the first adapter and which has a first engagement element with a terminal connection surface, and
a second adapter,
which is designed to be arranged on the shaft of the surgical instrument and which, in the docking situation, has an engaging element which faces the terminal connection surface and corresponds to it,
the connecting body of the first adapter forming a releasable connection with the corresponding engagement element of the second adapter in the docking situation,
wherein the terminal connection surface of the first adapter is inclined with respect to its longitudinal axis (Z) by a predetermined first angle (α) which lies in a range from 30° to 90°.

2. The docking device according to claim 1,
characterized in that
the connecting body of the first adapter is designed at least with its portion having the connection surface as a slide, and the corresponding engagement element of the second adapter is designed as a rail element for receiving the slide.

3. The docking device according to claim 1,
characterized in that
the connecting body forms a receptacle for a first laser device and has a first opening as an exit opening for a first laser beam,
and the elongated portion of the first adapter forms a receptacle for a second laser device and has a second opening as an exit opening for a second laser beam,
wherein the laser beam runs at a second angle (β) with respect to the longitudinal axis (Z) of the first adapter which is smaller than the first angle (α) and in a range from 20° to 80°, and wherein the first laser beam emerging from the opening intersects the second laser beam emerging from the second opening at a predetermined intersection point.

4. The docking device according to claim 3,
characterized in that
the first opening is a hole in the wall of the connecting body, a through-opening, or a cylindrical recess in the connecting body, the first opening preferably having edges beveled at an angle, and/or in that
the second opening is a hole in the wall of the first adapter, a through-opening, or a cylindrical recess in the first adapter, the second opening preferably having edges beveled at an angle, and/or the first opening preferably adjoining the terminal connection surface.

5. The docking device according to claim 1,
characterized in that
the corresponding engagement element of the second adapter is arranged over a tubular portion with a cylindrical passage opening of the second adapter through which the shaft of the surgical instrument can be guided.

6. The docking device according to claim 5,
characterized in that
the tubular portion has a coupling element which can be coupled to a corresponding coupling element at the proximal end of the shaft of the surgical instrument.

7. The docking device according to claim 1,
characterized in that
the first adapter has at its proximal end a second engagement element which is designed to be releasably connected to a corresponding engagement element of the holding arm.

8. The docking device according to claim 1,
characterized in that
the first adapter has at its proximal end a holding cone which tapers towards a proximal tip.

9. The docking device according to claim 1,
characterized in that
the docking device has a flange piece which is designed to be arranged on a corresponding mating flange of the holding arm, the flange piece preferably having a conical recess which corresponds with an outer circumferential shape of a holding cone to receive the holding cone.

10. A surgical holding device which has at least one holding arm which is connected via a docking device in a docking situation to a surgical instrument which has a rod-shaped shaft and a handle and is designed to be guided through a trocar, characterized in that the docking device is a docking device according to claim 1.

11. The surgical holding device according to claim 10, characterized in that the surgical holding device is a surgical robot with at least one robot head, the surgical robot having a control device for the controlled movement of the holding arm.

12. The surgical holding device according to claim 11, characterized in that the control device can be connected to a first laser device which is preferably arranged at the first opening, and to a second laser device which is preferably arranged at the second opening of the first adapter of the docking device, the laser devices being aligned with each other in such a way that their laser beams intersect at a predetermined intersection point, wherein the laser devices are laser fibers that can be connected to a laser beam source, or laser modules with their own laser beam source.

13. A method for connecting a holding arm of a surgical holding device, in a docking situation, by means of a docking device according to claim 1, with a surgical instrument which has a rod-shaped shaft and a handle and is designed to be guided via a trocar, comprising the steps of a) connecting the first adapter to the holding arm, b) arranging the second adapter on the surgical instrument, c) guiding the second adapter to the first adapter by moving the surgical instrument, and connecting the second adapter to the first adapter by engaging the terminal connection surface of the first engaging element of the first adapter with the first corresponding engaging element of the second adapter, thereby connecting the holding arm to the surgical instrument.

14. The method according to claim 13, wherein after step b) and before step c), the steps of b1) positioning the surgical instrument by inserting the shaft into the trocar, which is pivotably mounted about a predetermined pivot point, b2) by means of a first laser device arranged at the first opening of the first adapter, emitting a first laser beam in a predetermined direction and aligning the first laser beam with the pivot point by moving the holding arm and thus the first adapter, b3) by means of a second laser device arranged at the second opening of the first adapter, emitting a second laser beam in a predetermined direction which the first laser beam intersects at a predetermined intersection point, and aligning the second laser beam with the pivot point by moving the holding arm parallel to the first laser beam, thereby aligning the first adapter and consequently the holding arm with the pivot point.

15. The method according to claim 13, wherein before step a), step a0) is carried out, which provides for the attachment of a flange piece to the holding arm, and/or when the first adapter is connected in step a), piercing a sterile drape that surrounds at least the holding arm with the tip of the first adapter and/or clamping the sterile drape between the holding arm and the first adapter.

16. The method according to claim 13, wherein the connection of the surgical instrument to a holding arm is the connection of the surgical instrument to a holding arm of a surgical robot according to claim 11.

17. The method according to claim 16, comprising the steps of after step b2), carrying out step b2'), and blocking movements of the holding arm in the control device which do not take place parallel to the first laser beam, and/or after step b3), carrying out step b3'), and registering the pivot point by registering the intersection point of the first and second laser beams in the control device, and storing the registered pivot point in the control device in order to carry out controlled movements of the holding arm with respect to the registered pivot point.

* * * * *